(12) United States Patent
Kato (10) Patent No.: US 8,000,781 B2
(45) Date of Patent: Aug. 16, 2011

(54) METHOD OF EVALUATING EFFECT OF PROLONGING QT INTERVAL IN ELECTROCARDIOGRAM

(75) Inventor: Hiroshi Kato, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 562 days.

(21) Appl. No.: 12/097,642

(22) PCT Filed: Nov. 29, 2006

(86) PCT No.: PCT/JP2006/323767
§ 371 (c)(1),
(2), (4) Date: Jun. 16, 2008

(87) PCT Pub. No.: WO2007/069453
PCT Pub. Date: Jun. 21, 2007

(65) Prior Publication Data
US 2009/0234238 A1 Sep. 17, 2009

(30) Foreign Application Priority Data
Dec. 14, 2005 (JP) ................................. 2005-360698

(51) Int. Cl.
*A61B 5/04* (2006.01)
(52) U.S. Cl. ...................................................... 600/516
(58) Field of Classification Search .................. 600/516; 424/1.65, 145.1, 450; 514/248, 252.12
See application file for complete search history.

(56) References Cited

U.S. PATENT DOCUMENTS
4,756,904 A * 7/1988 Crook .......................... 424/1.65
2005/0215540 A1 * 9/2005 Marks et al. ............. 514/211.09

FOREIGN PATENT DOCUMENTS
JP 2005 533086 11/2005

OTHER PUBLICATIONS

Matsumoto, Yasunori et al., "Long-Term Endothelin A Receptor Blockade Inhibits Electrical Remodeling in Cardiomyopathic Hamsters", Circulation, vol. 106, pp. 613-619, (2002).
H. Katoh, el al. "Comparison of QT Interval in Several Experimental Animals and the Effects of E4031, Class I I I Antiarrhythmic Agent", The Journal of Toxicological Sciences, Proceedings of the 25th Annual Meeting, vol. 23, No. 4, 1998, p. 344 (P6-2).
Ivan Kocic, et al. "Regional and Frequency-Dependent Changes in Action Potentials and Transient Outward K+ Currents in Ventricular Myocytes from J-2-K Cardiomyopathic Hamsters", Basic Research in Cardiology, vol. 98, No. 6, 2003, pp. 367-379.

(Continued)

Primary Examiner — George Manuel
Assistant Examiner — Robert N Wieland
(74) Attorney, Agent, or Firm — Oblon, Spivak, McClelland, Maier & Neustadt, L.L.P.

(57) ABSTRACT

A method for evaluating electrocardiogram QT interval-prolonging action of a test substance, which comprises preparing a hamster anesthetized under such a condition that end of T wave is definitely observed on an electrocardiogram, and comparing electrocardiogram QT intervals of the hamster observed before and after administration of the test substance to evaluate electrocardiogram QT interval-prolonging action of the test substance.

11 Claims, 10 Drawing Sheets

OTHER PUBLICATIONS

Nobuya Matsuoka, et al. "Characterzation of Stress-Induced Sudden Death in Cardiomyopathic Hamsters", The Journal of Pharmacology and Experimental Therapeutics, vol. 284, No. 1, 1998, pp. 125-135.

Atsushi Takeda et al, "Three-Dimensional Distribution of Myocardial Fibrosis in the New J-2-N Cardiomyopathic Hamster: Comparison with Electrocardiographic Findings", Heart and Vessels, vol. 8, No. 4, 1993, pp. 186-193.

Takashi Kawashima, et al. "ECG Analysis of Golden Hamsters Exposed to Long Term-GZ Conditions: Ordinary and Pathological Findings" The Japanese Journal of Physiology, vol. 41, No. 4, 1991, pp. 629-651.

Osamu Hano, et al. "Arrhythmogenic Properties of the Ventricular Myocardium in Cardiomyopathic Syrian Hamster, BIO 14.6 Strain", Cardiovascular Research, vol. 25, 1991, pp. 49-57.

Hiroshi Tone, et al. "Effect of (2"R)-4'-0-Tetrahydropyranyladriamycin, A New Antitumor Antibiotic, On the Cardiac Function of Hamsters", The Japanese Journal of Antibiotics, vol. 39, Feb. 1986, pp. 547-568 (with an English Abstract thereof on the last page).

Tatsuo Hoshino et al, Electrocardiographic Abnormalities in Syrian Golden Hamsters with Coxsackievirus B, Myocarditis, Japanese Circulation Journal, vol. 46, Dec. 1982, pp. 1305-1312.

* cited by examiner

Control (Pre Drug)

E4031 10 μg/kg, iv 1 min

E4031 100 μg/kg, iv 1 min

E4031 1 mg/kg, iv 1 min

METHOD OF EVALUATING EFFECT OF PROLONGING QT INTERVAL IN ELECTROCARDIOGRAM

TECHNICAL FIELD

The present invention relates to a method for evaluating electrocardiogram QT interval-prolonging action.

BACKGROUND ART

Prolongation of the electrocardiogram QT interval by drugs has been currently concerned, and it is desired to evaluate whether a drug has or has not the action at an early stage of development of the drug, as it is also mentioned in the guideline of ICH. The electrocardiogram QT interval is the time from the start of the depolarization of the ventricle to the end of the repolarization thereof, and when the QT interval is prolonged by a drug or the like, polymorphic ventricular tachycardia of the type called torsades de pointes (TdP) may be induced. When this arrhythmia is induced, a fainting attack may be caused, and it may shift to ventricular fibrillation, which may be fatal one. As for the prolongation of the QT interval and the induction of TdP by drug administration, many reports have been made on antiarrhythmic drugs belonging to the class Ia according to the Vaugham Williams classification. However, in recent years, the prolongation of QT interval and induction of TdP are becoming to be reported for non-circulatory drugs including antibiotics such as erythromycin, antihistamines such as terfenadine and astemizole, and so forth. Furthermore, TdP may be induced by an interaction between drugs. Therefore, for all the compounds being developed as drugs for humans, it is necessary to examine the influence on the electrocardiogram QT interval as one of pharmacological safety tests.

Prolongation of the electrocardiogram QT interval means prolongation of the action potential duration of ventricular muscles. The ionic current participating in the repolarization of ventricular muscle action potential is a delayed rectifier potassium current ($I_K$), and if $I_K$ is suppressed, the action potential duration is prolonged. Most of the drugs which prolong the electrocardiogram QT interval are considered to suppress the HERG channel, which passes the rapid component of $I_K$ ($I_{Kr}$).

As for in vivo evaluation system for the prolongation of electrocardiogram QT interval, the evaluation is performed in anesthetized dogs and awaken dogs as a pharmacological safety test. However, use of dogs for in vivo evaluation of compounds under searching is difficult, in view of experimental technique and required amounts of compounds. Therefore, evaluation of electrocardiogram was investigated in smaller animals (Non-patent document 1). When E4031, which is considered to selectively suppress $I_{Kr}$, was examined by using anesthetized rabbits, guinea pigs, rats and mice, prolongation of the QT interval by E4031 was observed in rabbits and guinea pigs, whereas it was not observed in rats and mice.

It is considered that the reason why rats and mice cannot be used for evaluation of the QT interval is that the ion channel of them relating to the QT interval is different from that of humans, and it has also been considered that hamsters, which are also rodents, could not also be used for the evaluation.

Further, guinea pigs showed prolongation of the QT interval only in a small degree, and they were considered less sensitive. Rabbits showed high sensitivity and TdP-like ventricular tachycardia, and thus were considered favorably sensitive animals for the evaluation. However, they had a large body weight (about 2 kg), and therefore they were considered to be unsuitable for multi-specimen evaluation.

Non-patent document 1: J. Toxicol. Sci., 23, 344, 1998

DISCLOSURE OF THE INVENTION

As an in vivo evaluation system for the prolongation of electrocardiogram QT interval, supposing the evaluation at a explorative research stage in which the compounds are obtained only in small amounts, an evaluation system using a small animal is desired. Therefore, an object of the present invention is to provide a method for evaluating prolongation of electrocardiogram QT interval in vivo using a small animal.

The inventors of the present invention found that hamsters could be anesthetized under such a condition that the end of the T wave was definitely observed on an electrocardiogram, and measurement of the QT interval was thereby made easier, and that effects of E4031, an $I_{Kr}$ selective blocker, as well as terfenadine, an agent for allergic diseases, and cisapride, a prokinetic, of which QT interval-prolonging actions were clinically observed, on hamsters anesthetized under such a condition as mentioned above were similar to those observed in humans and anesthetized dogs, and thus accomplished the present invention.

The present invention provides a method for evaluating electrocardiogram QT interval-prolonging action of a test substance, which comprises preparing a hamster anesthetized under such a condition that end of T wave is definitely observed on an electrocardiogram, and comparing electrocardiogram QT intervals of the hamster observed before and after administration of the test substance to evaluate electrocardiogram QT interval-prolonging action of the test substance.

As for the anesthetization condition, for example, mixed anesthesia with pentobarbital and xylazine is used.

BRIEF DESCRIPTION OF THE DRAWINGS

FIG. 1-1 Electrocardiograms of a hamster anesthetized with pentobarbital alone, which include standard lead I electrocardiogram, lead II electrocardiogram, lead III electrocardiogram, lead VR electrocardiogram, lead VL electrocardiogram and lead VF electrocardiogram from the top (photographs of charts).

FIG. 1-2 Electrocardiograms of a hamster under mixed anesthesia with pentobarbital and xylazine, which include standard lead I electrocardiogram, lead II electrocardiogram, lead III electrocardiogram, lead VR electrocardiogram, lead VL electrocardiogram and lead VF electrocardiogram from the top (photographs of charts).

FIG. 2 Standard lead electrocardiograms of a hamster under mixed anesthesia with pentobarbital and xylazine (photographs of charts)
a) Standard limb lead electrocardiogram recorded with an electrocardiograph for humans, including standard lead I electrocardiogram (LI), standard lead II electrocardiogram (LII) and standard lead III electrocardiogram (LIII) from the top.
Amplifier high frequency characteristic: 35 Hz (−3 dB under the condition of on-state of myoelectric filter)
Recorder frequency characteristic: 0.05 to 100 Hz (−3 dB), sensitivity: 20 mm/mV.
b) Standard lead II electrocardiogram measured and recorded with a biological amplifier and a thermal array recorder. Frequency characteristic of biological amplifier: 0.08 to 300 Hz, Frequency characteristic of thermal array recorder: DC up to 2.8 kHz, sensitivity: 70 mm/mV.

The broken line in the electrocardiogram indicates the positions of the starting point of QRS, and the end of the T wave before E4031 administration.

FIG. 7-1 Influence of terfenadine on the electrocardiogram parameters in a hamster under mixed anesthesia with pentobarbital and xylazine.

The black triangles and white circles indicate the results obtained with terfenadine and those of control, respectively, each value is indicated as average±standard error for 5 examples, and * means $p<0.05$ vs. control.

FIG. 7-2 Influence of cisapride on the electrocardiogram parameters in a hamster under mixed anesthesia with pentobarbital and xylazine.

The black squares and white circles indicate the results obtained with cisapride and those of control, respectively, each value is indicated as average±standard error for 5 examples, and * means $p<0.05$ vs. control.

FIG. 7-3 Influence of E4031 on the electrocardiogram parameters in a hamster under mixed anesthesia with pentobarbital and xylazine.

The black circles and white circles indicate the results obtained with E4031 and those of control, respectively, each value is indicated as average±standard error for 5 examples, and * means $p<0.05$ vs. control.

BEST MODE FOR CARRYING OUT THE INVENTION

The evaluation method of the present invention is characterized by comprising preparing a hamster anesthetized under such a condition that end of the T wave is definitely observed on an electrocardiogram, for example, anesthetized with a combination of pentobarbital and xylazine, and comparing electrocardiogram QT intervals of the hamster observed before and after administration of a test substance to evaluate electrocardiogram QT interval-prolonging action of the test substance.

Although the hamster used in the evaluation method of the present invention is not particularly limited, it is preferable to use a hamster supplied as an experimental animal in view of breeding and management. Although the hamster to be used is not particularly limited so long as a hamster grown up to an extent suitable for the measurement of electrocardiogram is used, it is usually 4- to 30-week old hamster.

For the anesthetization, a condition enabling observation of a definite end of the T wave in an electrocardiogram and thus enabling measurement of QT interval may be used. Such a condition may be selected on the basis of no increase of the heart rate. For example, in the case of pentobarbital anesthetization, anesthetization with pentobarbital alone makes sympathetic nerve activity relatively higher, and invites a high heart rate state. Thus, end of the T wave overlaps the next P wave, and determination becomes difficult. Therefore, anesthetization with pentobarbital alone is not suitable for measurement of the electrocardiogram QT interval. On the other hand, mixed anesthesia with pentobarbital and xylazine decreases heart rate compared with anesthetization with pentobarbital alone, which results in separation of end of the T wave and the next P wave, and makes the end of the T wave definite in an electrocardiogram, and therefore it enables measurement of the QT interval.

Although the anesthetization condition is not particularly limited so long as a condition that makes end of the T wave definite in an electrocardiogram and thus enables measurement of the QT interval is chosen, specific examples of the anesthetization method include, for example, mixed anesthesia with pentobarbital and xylazine, mixed anesthesia with ketamine and xylazine, urethane anesthetization, α-chloralose anesthetization, inhalation anesthesia with halothane or isoflurane, and so forth, and preferably, mixed anesthesia with pentobarbital and xylazine is desirable. Pentobarbital may be, for example, intraperitoneally administered at a dose of 30 to 70 mg/kg. Xylazine may be, for example, intramuscularly injected at a dose of 1 to 3 mg/kg.

For the mixed anesthesia with ketamine and xylazine among the aforementioned anesthetization methods, it has been reported that 1.0 mg/kg iv of xylazine decreases heart rate of dogs, and 10 mg/kg iv ketamine thereafter transiently increases the heart rate to a level higher than that observed before the xylazine administration, but thereafter gradually it decreases to and settles at a level around the level observed before the xylazine administration (Haskins S. C., Patz J. D., and Farver T. B., "Xylazine and xylazine-ketamine in dogs", Am. J. Vet. Res., 47, 636-641, 1986). Therefore, it can be used for the method of the present invention.

Further, although Pettinger et al. reported that urethane anesthetization tends to slightly increase heart rate in rats, the increase of heart rate is smaller than that observed with pentobarbital, which is compared at a time (Pettinger W. A., Tanaka K., Keeton K., Campbell W. B., and Brooks S. N., "Renin release, an artifact of anesthesia and its implications in rats", Proc. Soc. Exp. Biol. Med., 148, 625-630, 1975). Therefore, urethane anesthetization can also be used for the method of the present invention.

As for the α-chloralose anesthetization, there are a report that it does not influence on the heart rate (Marullaz R. D., Combre A., and Boucher M., "Comparison of the effects of pentobarbital and chloralose on the cardiac rhythms of the dog in chronic atrio-ventricular heart block", Eur. J. Pharmacol., 32, 393-395, 1975) and a report that it increases the heart rate (Boucher M., Dubray C., Li J. H., Paire M., and Duchene-Marullaz P., "Influence of pentobarbital and chloralose anesthesia on quinidine-induce effects on atrial refractoriness and heart rate in the dog", J. Cardiovasc. Pharmacol., 17, 199-206, 1991). However, even in the latter report, the increase of heart rate is also smaller than that observed with pentobarbital, and therefore it can be used for the method of the present invention.

Further, halothane and isoflurane are reported to have, as a direct action on the sinoatrial node, an action of suppressing automaticity, i.e., an action of decreasing heart rate (Bosnjak Z. J., and Kampine J. P., "Effects of halothane, enflurane, and isoflurane on the SA node", Anesthesiol., 58, 314-321, 1983), and therefore it can also be used for the method of the present invention.

Although the leads for the measurement of electrocardiogram are not particularly limited, leads on body surface are preferred, and the standard limb lead I or II, or the unipolar limb lead VR is more preferred, and the standard limb lead II is especially preferred.

Although the body position of the hamster at the time of the measurement is not particularly limited, the dorsal position or ventral position is preferred, and the dorsal position is still more preferred.

The apparatus used for the measurement of electrocardiogram may be a usual electrocardiograph provided that measurement conditions such as sensitivity and frequency characteristics are adjusted to those for electrocardiogram measurement of hamster. The electrocardiograph may be a commercially available one, or may be constituted together with an amplifier or a recorder. Preferred characteristics of the apparatus include sensitivity of 10 to 100 mm/mV and frequency characteristic of −6 dB at 0.08 Hz to 1 kHz.

Electrocardiography of a hamster has been reported in Basic Res. Cardiol., 98, 367-379, 2003; J. Pharmacol. Exp. Ther., 284, 125-135, 1998; Heart Vessels, 8, 186-193, 1993; Jap. J. Physiol., 41, 629-651, 1991; Cardiovas. Res., 25, 49-57, 1991; Jap. J. Antibio., 34, 231-252, 1986; Jap. Cir. J., 46, 1305-1312, 1982 and so forth. When the waveforms in the electrocardiograms mentioned in the aforementioned references and the waveforms in the electrocardiograms recorded in the examples described later were compared, difference in waveforms of the P wave was not observed. However, no reference refers to bifidity of the R wave. Although the references may not describe electrocardiography conditions, it is considered that most of the electrocardiographies were performed with electrocardiographs for humans. In the examples described later, no bifidity of the R wave was observed with an electrocardiograph for humans, but bifid R waves were recorded when a biological amplifier and a thermal array recorder of favorable frequency characteristics were used in combination. Therefore, it is considered that the difference in waveform of the R wave is due to difference of recording conditions. Although the waveform of the R wave may be different depending on measurement conditions as described above, the measurement conditions are not limited so long as the electrocardiogram QT interval can be measured in a hamster under mixed anesthesia.

The measurement of the electrocardiogram QT interval and administration of a test substance may be performed according to usual methods. Usually, by preparing a hamster under mixed anesthesia with pentobarbital and xylazine, measuring the electrocardiogram QT interval of the hamster, administering a test substance to the hamster, and measuring the electrocardiogram QT interval of the hamster after the administration, electrocardiogram QT intervals of the hamster observed before and after the administration of the test substance can be obtained. By comparison of the electrocardiogram QT intervals of the hamster observed before and after the administration, electrocardiogram QT interval-prolonging action of the test substance can be evaluated.

Moreover, in order to take variation among tests into consideration, it is preferable to use a positive control for the evaluation. Substance used as the positive control is not particularly limited so long as a substance known to have an electrocardiogram QT interval-prolonging action is used, and examples include, for example, E4031.

Hereafter, the present invention will be explained in more detail with reference to examples. These examples shows examples of implementation of the present invention, and the present invention is not limited by these examples. The abbreviations used in the following descriptions are similar to the abbreviations conventionally used in this field.

Example 1

1. Animals, Reagents and Instruments 1.1. Animals Used

Syrian hamsters (weight: 122 to 150 g, age in week: 7 or 9 to 10 week-old) were used.

The hamsters were purchased from Japan SLC, Inc. (Hamamatsu, Shizuoka). They were preliminarily bred under controlled temperature (23±2° C.), humidity (55±10% RH), and illumination (lighting and darkness for 12 hours each), and then used for the experiment. During the breeding, the animals were fed with chows for experimental animals MF (Oriental Yeast Co., Ltd., Tokyo) and tap water ad libitum.

1.2. Test Substance and Reagents 1.2.1. E4031

E4031 was dissolved in physiological saline and intravenously administered.

Dose was 1 to 1000 μg/kg (1 mL/kg).

[Formula 1]

·2HCl·2H₂O 1.2.2. Other Reagents

Pentobarbital sodium (Nembutal (registered trademark)) used for the anesthetization of the animals was purchased from Dainippon Pharmaceutical Co., Ltd. (Osaka). Xylazine hydrochloride (Celactal (registered trademark)) was purchased from Bayer Ltd. (Tokyo). Celactal (registered trademark) was used as a 20 mg/mL solution in terms of xylazine, and upon administration, it was diluted 20 times with physiological saline and intramuscularly injected at a dose of 1 mg/kg (1 mL/kg).

1.3. Instruments and Equipments

Limb-lead electrocardiograms (standard limb lead and unipolar limb lead) were measured and recorded by using an electrocardiograph (ECG-6403, Nihon Kohden Corp., Tokyo), or measured by using a bioelectric amplifier (AB-651J (S-1516), Nihon Kohden Corp., Tokyo) and recorded on a thermal array recorder (WS-682G, Nihon Kohden Corp., Tokyo). In the cases of using atrial pacing, artificial respiration was carried out by using a respirator for small animals (SAR-830P, CWE Inc., Ardmore, Pa., USA) under the conditions of tidal volume: 3 mL and frequency of respiration: 30 times/minute. For the atrial pacing, an electrostimulator (SEN-7203682G, Nihon Kohden Corp., Tokyo) and an isolator (SS-403J, Nihon Kohden Corp., Tokyo) were used, and stimulation was performed with a rectangular wave having a width of 1 ms and a magnitude twice the threshold.

2. Methods and Results 2.1. Examination on Electrocardiography

Figure 11:
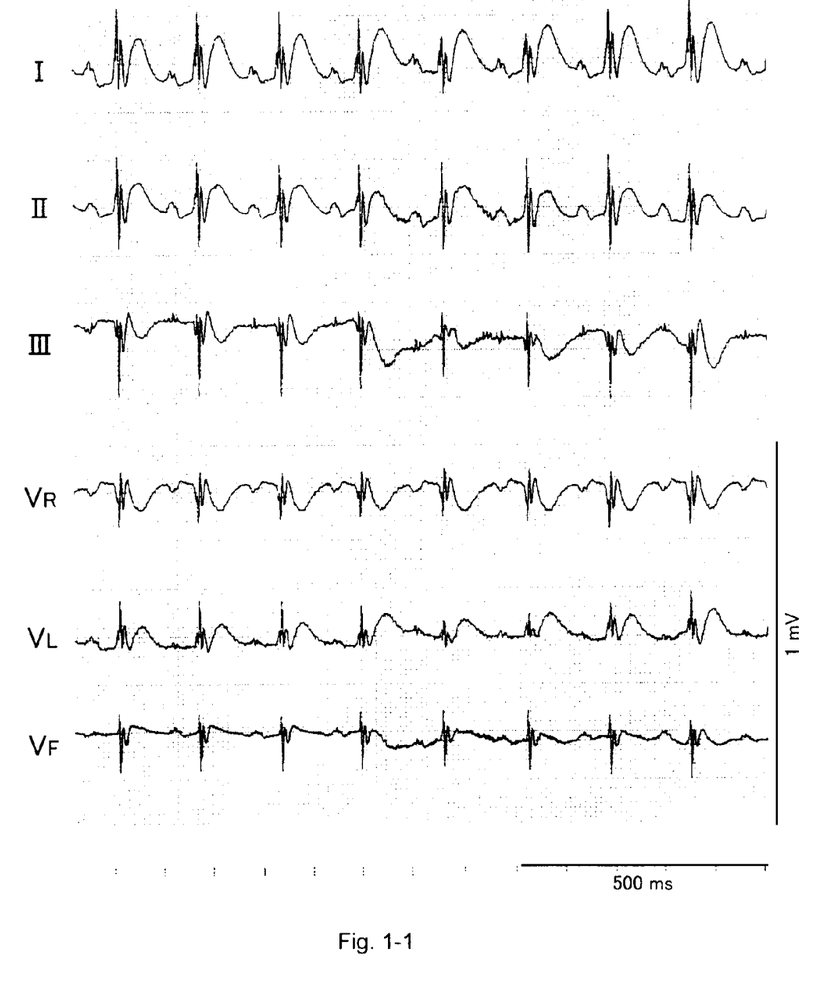

The hamsters were anesthetized with 50 mg/kg ip of pentobarbital sodium, and waveforms of electrocardiogram recorded for a hamster in the dorsal position are shown in FIG. 1-1. These waveforms of electrocardiogram were recorded by using the bioelectric amplifier and the thermal array recorder. Although the leads with which each wave on an electrocardiogram was clearly recorded were the standard limb leads I and II and the unipolar limb lead VR, the standard limb lead I was likely to be influenced by respiration (5th and 6th beats in FIG. 1-1), and in the unipolar limb lead VR, the polarity was conversely recorded, which made reading difficult. Therefore, the lead enabling easy evaluation of the parameters on the electrocardiogram was the standard limb lead II (standard lead II electrocardiogram). However, the end of the T wave overlapped the P wave (waveforms will be described later) with these leads, and therefore measurement of the QT interval was impossible.

Figure 12:
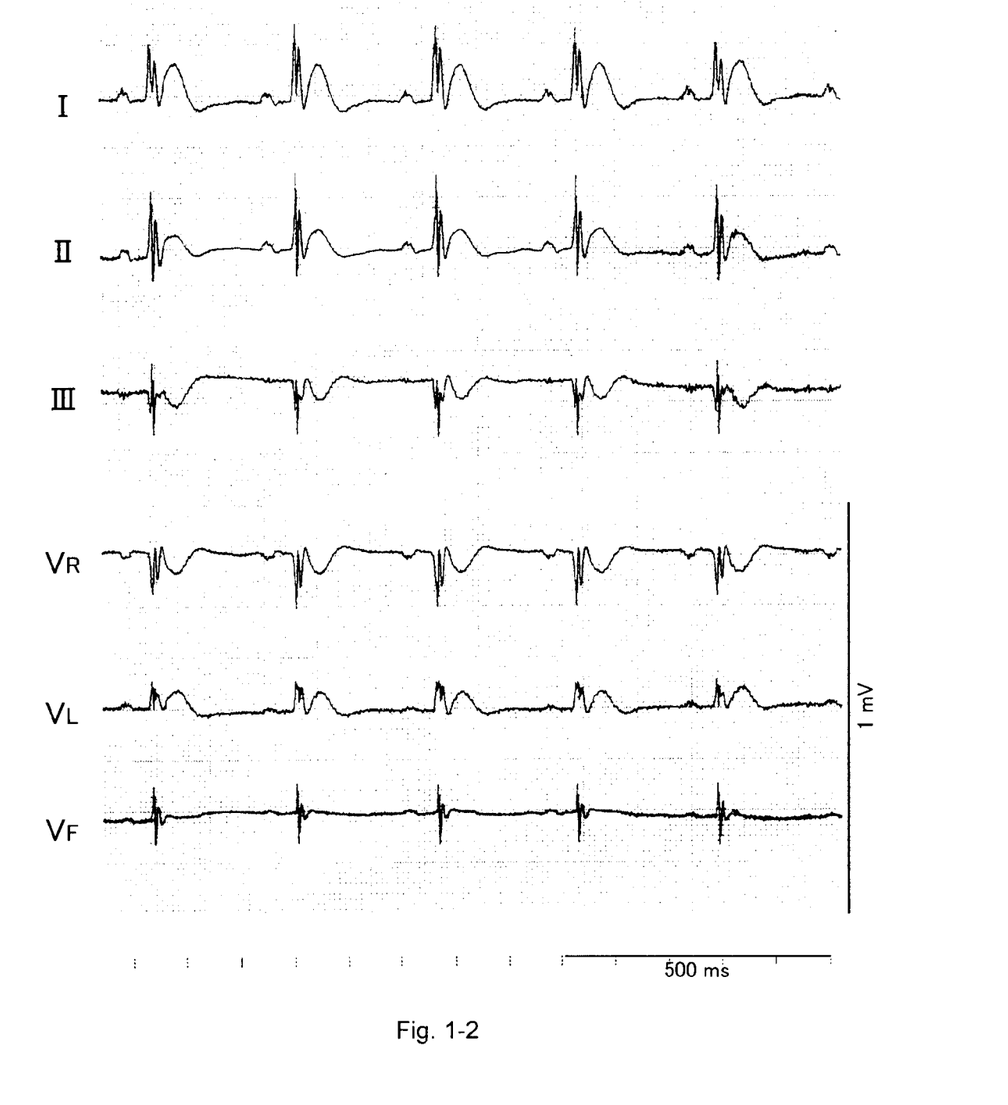

Waveforms of electrocardiogram of the animal obtained after intramuscular injection of 2 mg/kg of xylazine are shown in FIG. 1-2. The administration of xylazine decreased the heart rate, i.e., prolonged the RR interval, thus the end of the T wave became definite, and the QT interval became measurable. Therefore, it was decided to perform the following examination by using mixed anesthesia with pentobarbital and xylazine.

Then, electrocardiography was performed with changing the position of the animal to investigate influence of the position on the waveforms of electrocardiogram. Although not shown in the drawing, any change was not observed on the electrocardiogram even when the position was changed from the dorsal position to the ventral position. When the animal was made in the right lateral position, the T wave became diphasic, and it became difficult to determine the end of the T wave. When the animal was made in the left lateral position, increase of the S wave was observed in the standard limb leads I and II. It was decided to perform recording with the dorsal position in view of easy observation of the end of the T wave and ease of operation.

Figure 2:
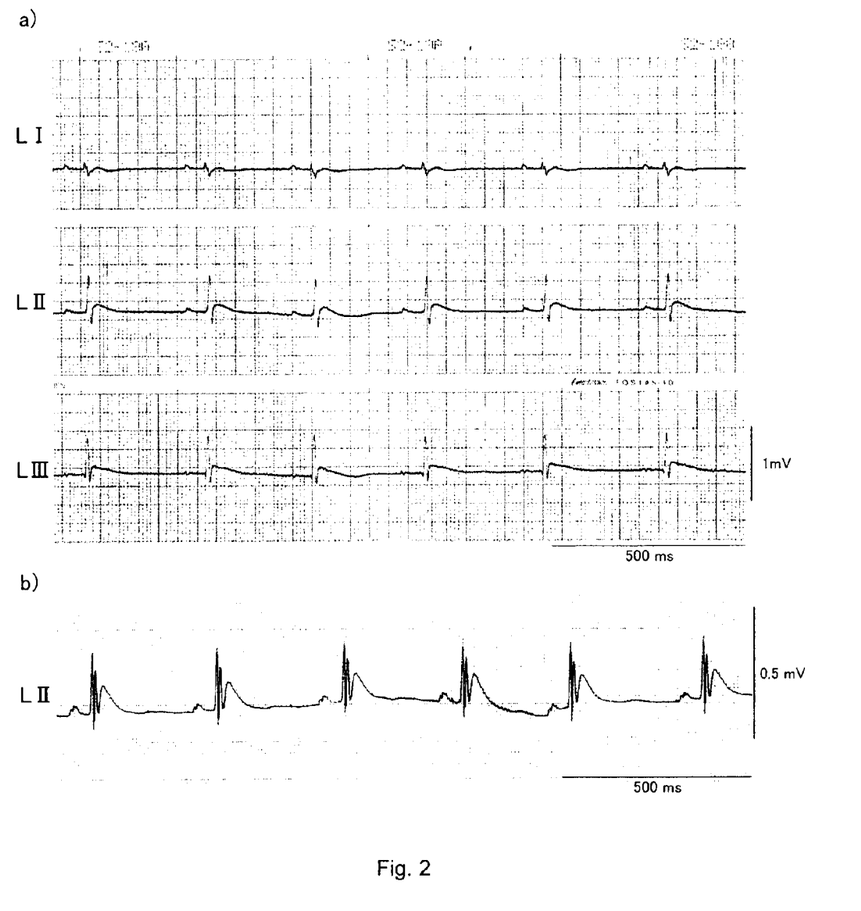

The difference of electrocardiogram due to the difference of the measurement apparatus of electrocardiograph is shown in FIG. 2. A standard lead electrocardiogram recorded by using an electrocardiograph for humans is shown on the top, and waveforms of a standard lead II electrocardiogram measured and recorded by using the biological amplifier and the thermal array recorder is shown on the bottom. Since the electrocardiograph for humans had low frequency characteristics, i.e., an amplifier high frequency characteristic of 35 Hz (−3 dB under on-state of myoelectric filter) and a recorder high frequency characteristic of 100 Hz (−3 dB), it could not record bifidity of the R wave, either. Moreover, due to the low sensitivity as low as 20 mm/mV, it was also difficult to read the starting points and end points of the P wave and the T wave. Therefore, the electrocardiography was performed by using the biological amplifier and the thermal array recorder, which had characteristics suitable for electrocardiography of hamsters.

2.2. Characteristics of Waveforms of Hamster Electrocardiogram

Figure 3:
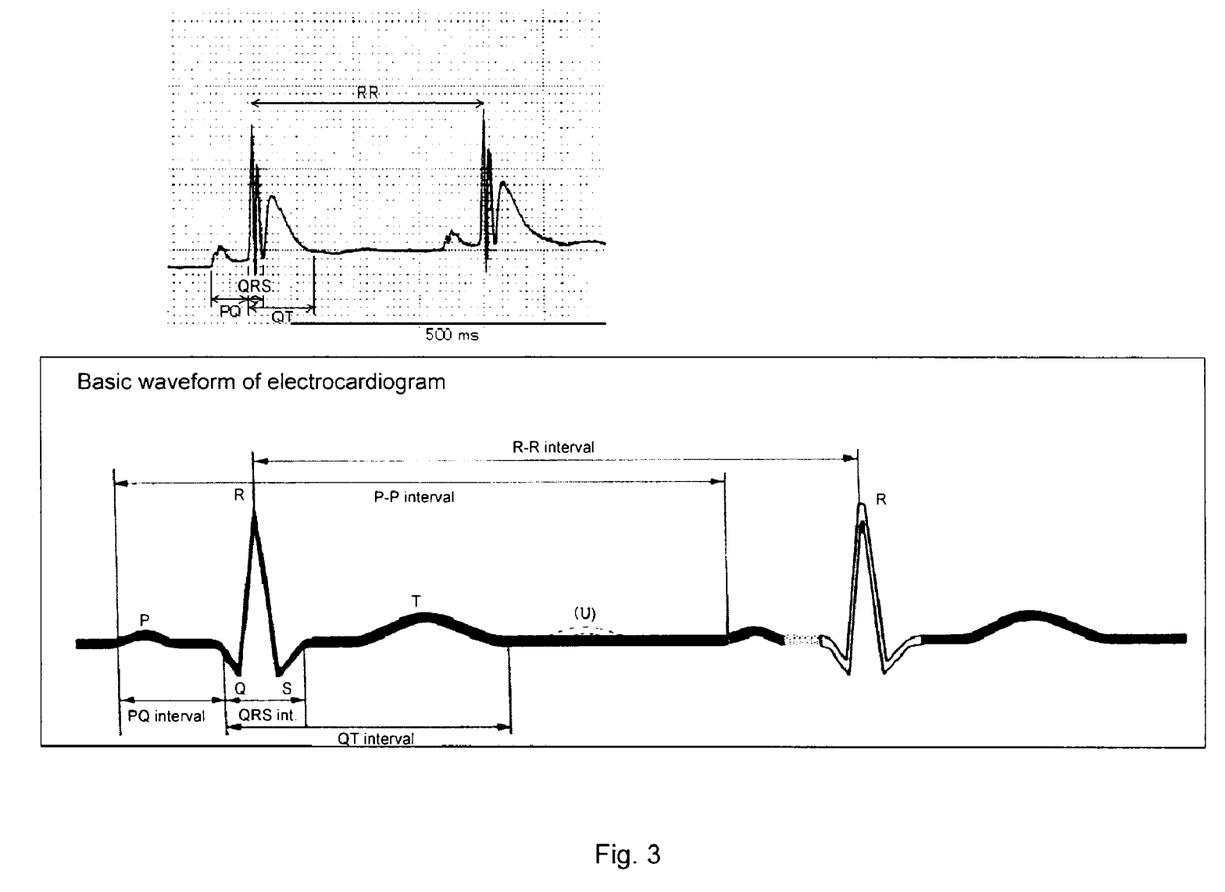
FIG. 3 Standard lead II electrocardiogram of a hamster under mixed anesthesia with pentobarbital and xylazine (top) and basic waveform in human electrocardiogram (bottom) (photographs of charts).

Waveforms of standard lead II electrocardiogram and the measurement parameters are shown on the top of FIG. 3. Electrocardiogram waveforms of human are schematically shown on the bottom. These drawing were depicted by using substantially the same time axis. The characteristics of the electrocardiogram of hamster (standard lead II electrocardiogram) were as follows.

(1) The Q wave is not observed (the Q wave is not observed in a standard lead II electrocardiogram of a normal human, either).
(2) The R wave shows bifidity.
(3) The S wave is not observed.
(4) The peak of the T wave is near the R wave.
(5) The wave returns from the end of the T wave to the base line in a gentle slope.
(6) The RR interval is short.

Therefore, measurement of the parameters on the electrocardiogram was performed for the followings.
PQ interval (or PQ time): from the starting point of the P wave to the starting point of the R wave
QRS interval (or QRS duration): from the starting point to the end point of the R wave
QT interval (or QT time): from the starting point of the R wave to the end point of the T wave In the following examination, although an average of values of contiguous three beats was basically used as a value of parameter at a certain time point, an average of values of two beats or four beats or a value of one beat may also be used.

2.3. Examination on Properties of Electrocardiogram QT Interval

Figure 4:
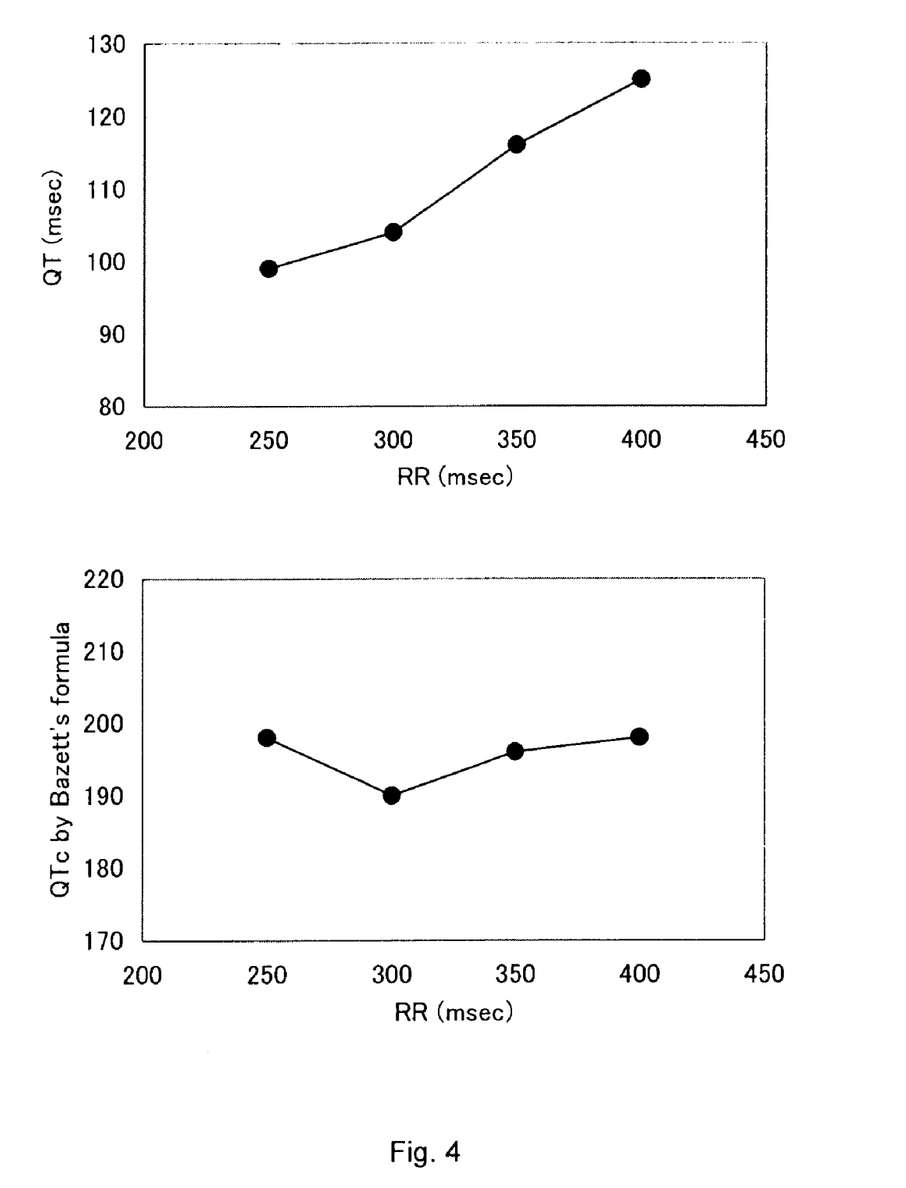
FIG. 4 Relationship between electrocardiogram QT interval and RR interval in a hamster under mixed anesthesia with pentobarbital and xylazine (n=1).

Heart rate dependency of the QT interval was examined. It is known that if the heart rate increases (RR interval shortens), the QT interval shortens in dogs, rabbits and guinea pigs. A hamster was thoracotomized under mixed anesthesia with pentobarbital and xylazine, and a standard lead II electrocardiogram was recorded to measure the QT interval while shortening the RR interval by atrial pacing. Since the RR interval at the time of sinus rhythm was 400 ms, the cycle length of the pacing was shortened from 400 ms to 250 ms by a step of 50 ms. The length of 200 ms corresponded to the absolute refractory phase, and the pacing was impossible. The pacing at each cycle length was performed for 30 seconds or longer, and then the standard lead II electrocardiogram was recorded. The relationship between the QT interval and the RR interval obtained in the recording is shown on the top of FIG. 4.

When the pacing cycle length was shortened to shorten the RR interval, the QT interval was also shortened. The QT interval was influenced by the RR interval also in humans, and in order to correct it, the Bazett's correction formula ($QTc = QT/\sqrt{(RR(s))}$) was used. The QTc interval corrected by using the Bazett's correction formula is shown on the bottom of FIG. 4. It is considered that the correction based on the Bazett's formula is relatively effective in this example. Therefore, in a hamster under mixed anesthesia with pentobarbital and xylazine, if the RR interval is shortened, the QT interval is shortened, and it can be said that this characteristic is qualitatively similar to that observed in dogs, rabbits and guinea pigs.

Figure 5:
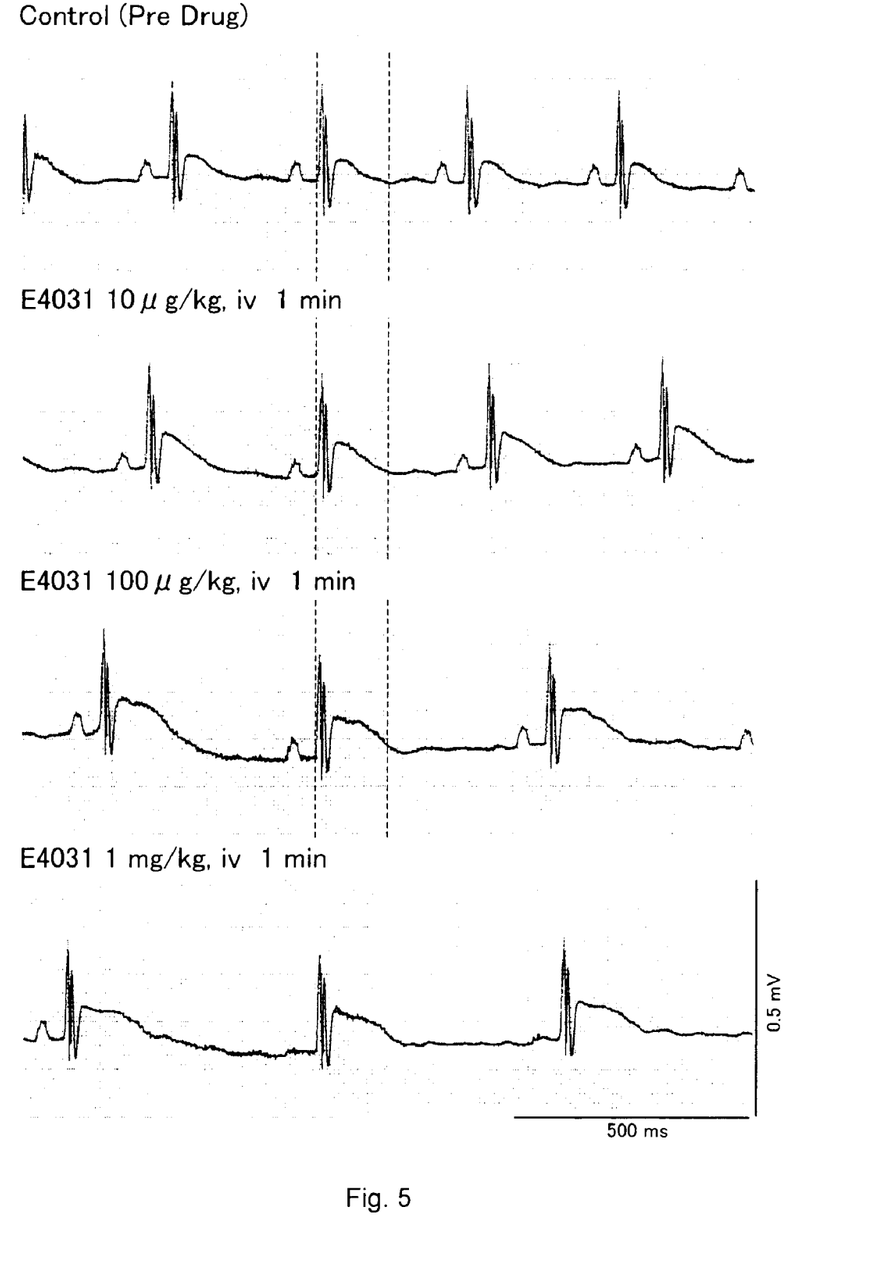
FIG. 5 Influence of E4031 on electrocardiogram in a hamster under mixed anesthesia with pentobarbital and xylazine (photograph of chart).

Then, influence of E4031 which selectively blocks $I_{Kr}$, the rapid component of delayed rectifier outward potassium current, was examined. It is considered that the main factor of the drug-induced QT prolongation in humans is $I_{Kr}$ block. In the case of animals, it is known that, with E4031, prolongation of the QT interval is observed in dogs, rabbits and guinea pigs, whereas the QT prolongation is not observed in mice and rats. A standard lead II electrocardiogram of a hamster under mixed anesthesia with pentobarbital and xylazine observed after intravenous administration of E4031 is shown in FIG. 5. E4031 was intravenously administered via a cannula indwelled in the external jugular vein. The doses were 10, 100 and 1000 μg/kg, and intravenous administration was performed at intervals of 10 minutes. Each record in FIG. 5 is a standard lead II electrocardiogram measured 1 minute after the administration. Prolongation of the QT interval was observed after the administration of 10 µg/kg, and the QT interval was further prolonged after the administration at 100 µg/kg. After the administration of 1 mg/kg, the P wave disappeared, and it was judged that sinoatrial block arose.

Figure 6:
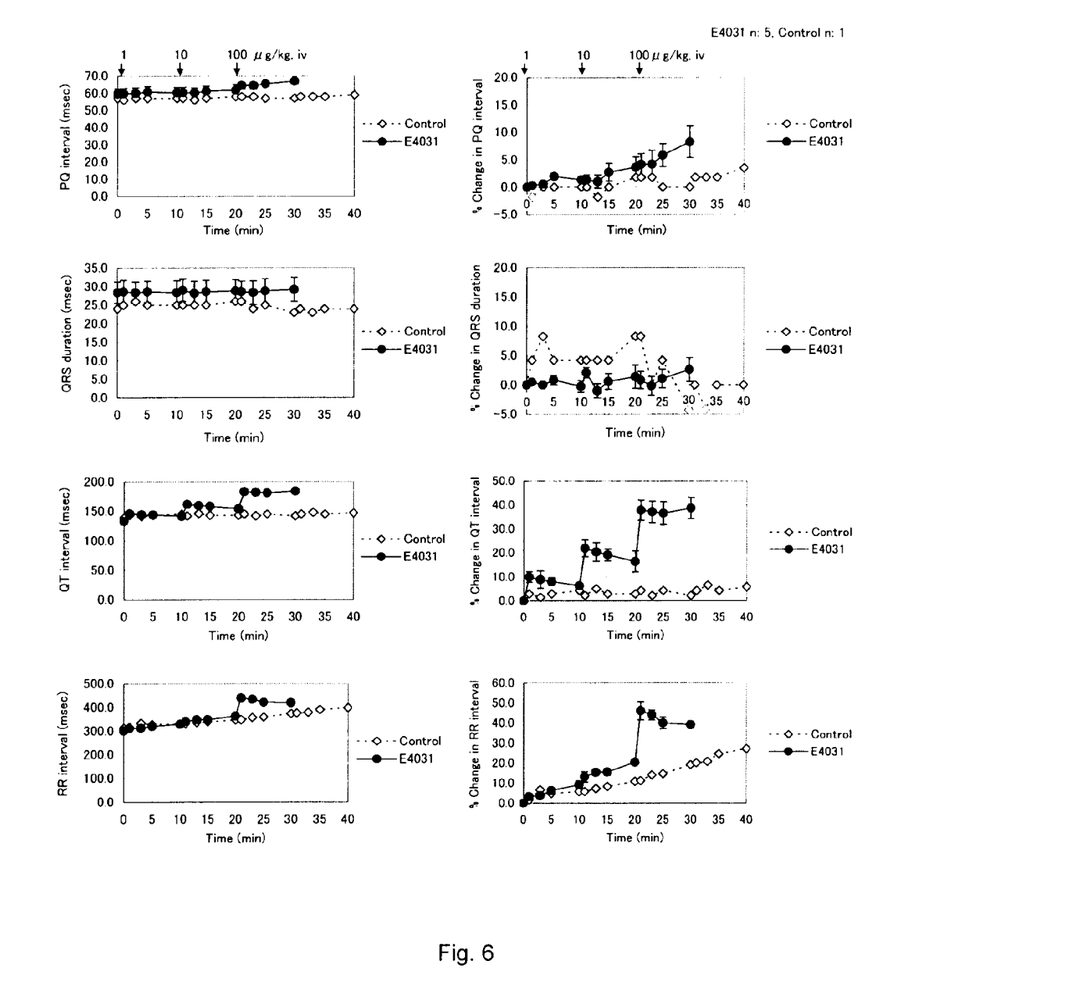
FIG. 6 Influence of E4031 on electrocardiogram parameters in a hamster under mixed anesthesia with pentobarbital and xylazine.

Examination of influence of E4031 on the electrocardiogram parameters was performed in five hamsters with a decreased minimum dose of 1 µg/kg, and the results are summarized in FIG. 6. The results are indicated with absolute values in the left graph, and indicated with percentages of change based on the values observed before the administration in the right graph. Since only one example was used for the control, which was intravenously administered only with physiological saline, statistical analysis was not conducted. After the administration of 1 mg/kg of E4031, sinoatrial block was observed in all the examples, and therefore measurement of the electrocardiogram parameters was not performed. Although E4031 slightly prolonged the PQ interval at 100 µg/kg, it was change of about 10%, and it was not considered to be significant influence. It did not substantially influence on the QRS interval. On the other hand, it showed marked prolongation action on the QT interval. Although statistical analysis was not performed, about 10% of prolongation was observed at 1 µg/kg. Moreover, prolongation of the RR interval was also observed at a dose of 10 µg/kg or higher.

These results revealed that the electrocardiogram QT interval of a hamster under mixed anesthesia with pentobarbital and xylazine had properties that it shortened as the RR interval shortened, and prolonged by $I_{Kr}$ block. These properties are similar to those observed in humans, dogs, rabbits and guinea pigs, and differs from those observed in mice or rats.

Comparing degree of this prolongation of the QT interval in a hamster under the mixed anesthesia with the previously reported results for of anesthetized guinea pigs, anesthetized rabbits and anesthetized and awaken dogs (Folia Pharmacol. Jpn., 121, 384-392, 2003), the sensitivity of the anesthetized hamster was higher than that of anesthetized guinea pigs, and comparative to that of anesthetized rabbits or anesthetized dogs. However, induction of TdP-like arrhythmia was not observed as in anesthetized rabbits. Therefore, it is considered that a hamster under mixed anesthesia with pentobarbital and xylazine can serve as an evaluation system for detecting the $I_{Kr}$ blocking action. Further, prolongation of the QT interval was observed from a dose that did not induce prolongation of the RR. Therefore, an advantage was recognized that the evaluation could be performed under a condition that influence of the RR interval on the QT interval need not be considered.

Example 2

Influence of Terfenadine, Cisapride and E4031 on Electrocardiogram QT Interval in Hamster Under Mixed Anesthesia with Pentobarbital and Xylazine 1. Experimental Methods
1.1. Animals Used Syrian hamsters (weight: 90 to 119 g, age in week: 6 or 7 week-old) were used.

The hamsters were purchased from Japan SLC, Inc. (Hamamatsu, Shizuoka). They were preliminarily bred under controlled temperature (23±2° C.), humidity (55±10% RH), and illumination (lighting and darkness for 12 hours each), and then used for the experiment. During the breeding, the animals were fed with chows for experimental animals MF (Oriental Yeast Co., Ltd., Tokyo) and tap water ad libitum.

1.2. Test Substances and Reagents
1.2.1. Terfenadine

A 10% $PEG_{200}$ solution was used as a solvent, and hydrochloric acid was added in an amount slightly larger than the equimolar amount for dissolution.

Administration method was intravenous administration, and dose was 10 to 1000 µg/kg (1 mL/kg).

[Formula 2]

1.2.2. Cisapride

A 10% $PEG_{200}$ solution was used as a solvent, and citric acid was added in a 2- to 3-fold molar amount for dissolution.

Administration method was intravenous administration, and dose was 1 to 100 µg/kg (1 mL/kg).

[Formula 3]

1.2.3. E4031

E4031 was dissolved in a 10% $PEG_{200}$ solution, and intravenously administered.

Dose was 1 to 100 µg/kg (1 mL/kg).

[Formula 4]

·2HCl·2H₂O 1.2.4. Other Reagents

The other reagents were the same as those used in Example 1.

1.3. Instruments and Equipments

A standard lead II electrocardiogram was measured by using a bioelectric amplifier (AB-651J (S-1516), Nihon Kohden Corp., Tokyo) and recorded on a thermal array recorder (WS-682G, Nihon Kohden Corp., Tokyo).

1.4. Experimental Procedure

The hamsters were anesthetized with 50 mg/kg ip of pentobarbital sodium, and then intramuscularly injected with 1 mg/g of xylazine at the hind leg. Each animal was fixed on the dorsal position, and a lead II electrocardiogram was measured with needle electrodes pierced into the right forelimb and both hind legs. The cervix skin was cut open, and a cannula was indwelled in the external jugular vein for intravenous administration. Terfenadine was intravenously administered at 10, 100 and 1000 μg/kg, and cisapride and E4031 were intravenously administered at 1, 10 and 100 μg/kg, at intervals of about 10 minutes for all the substances. The control group was intravenously administered 3 times with 1 mL/kg of a 10% $PEG_{200}$ solution at intervals of 10 minutes. Five animals were used for each of the terfenadine administration group, the cisapride administration group, the E4031 administration group and the control group, and thus 20 animals were used in total. The animals were randomly assigned to each group only in consideration of the number of animals.

1.5 Experimental Data Analysis

For statistical test, a statistical analysis support system incorporating SAS 6.12 (SAS Institute Japan, Inc., Tokyo) was used. As analysis of the parameters on electrocardiograms, repeated measures ANOVA was performed, and then unpaired t-test was carried out to perform comparison with the control group for the same time point. When P was smaller than 0.05 ($P<0.05$), it was determined there was significant difference.

2. Results

Figure 71:
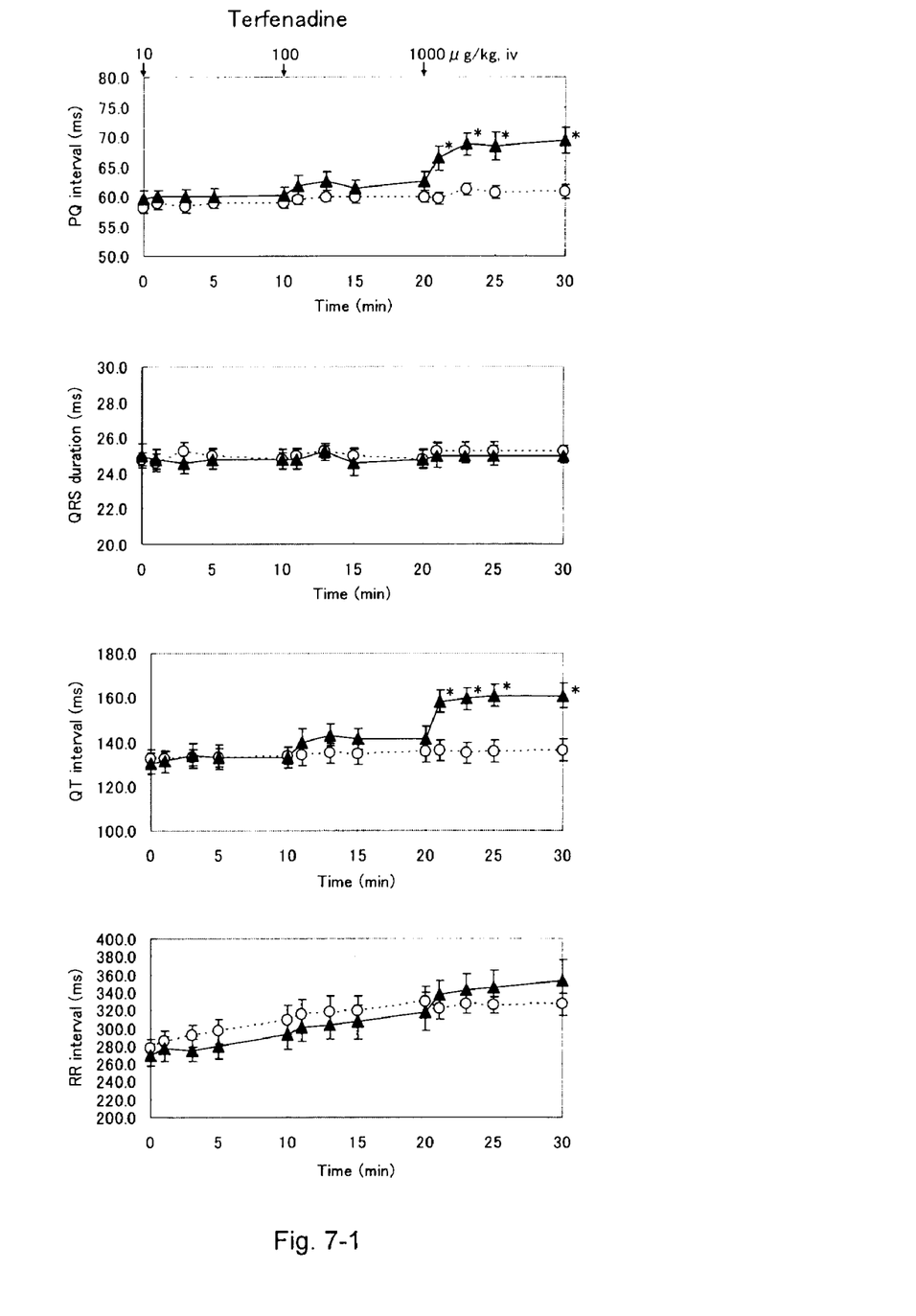
Figure 72:
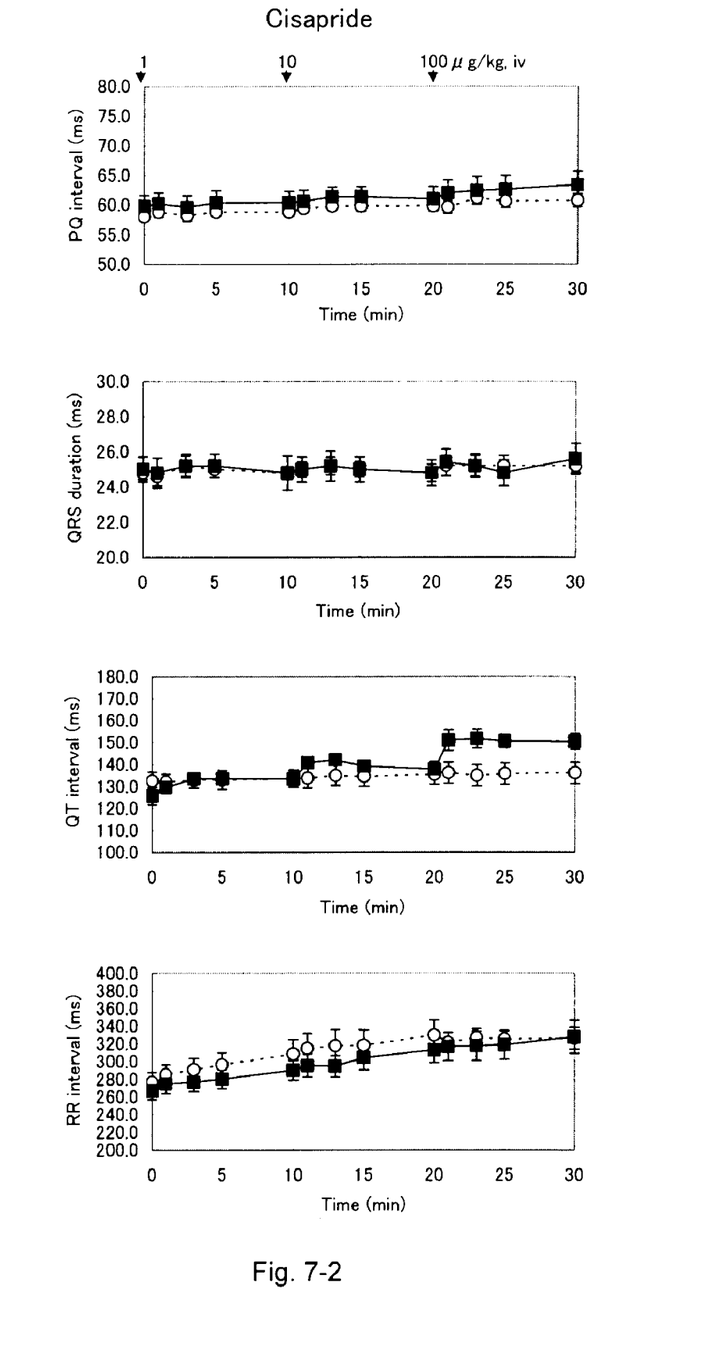
Figure 73:
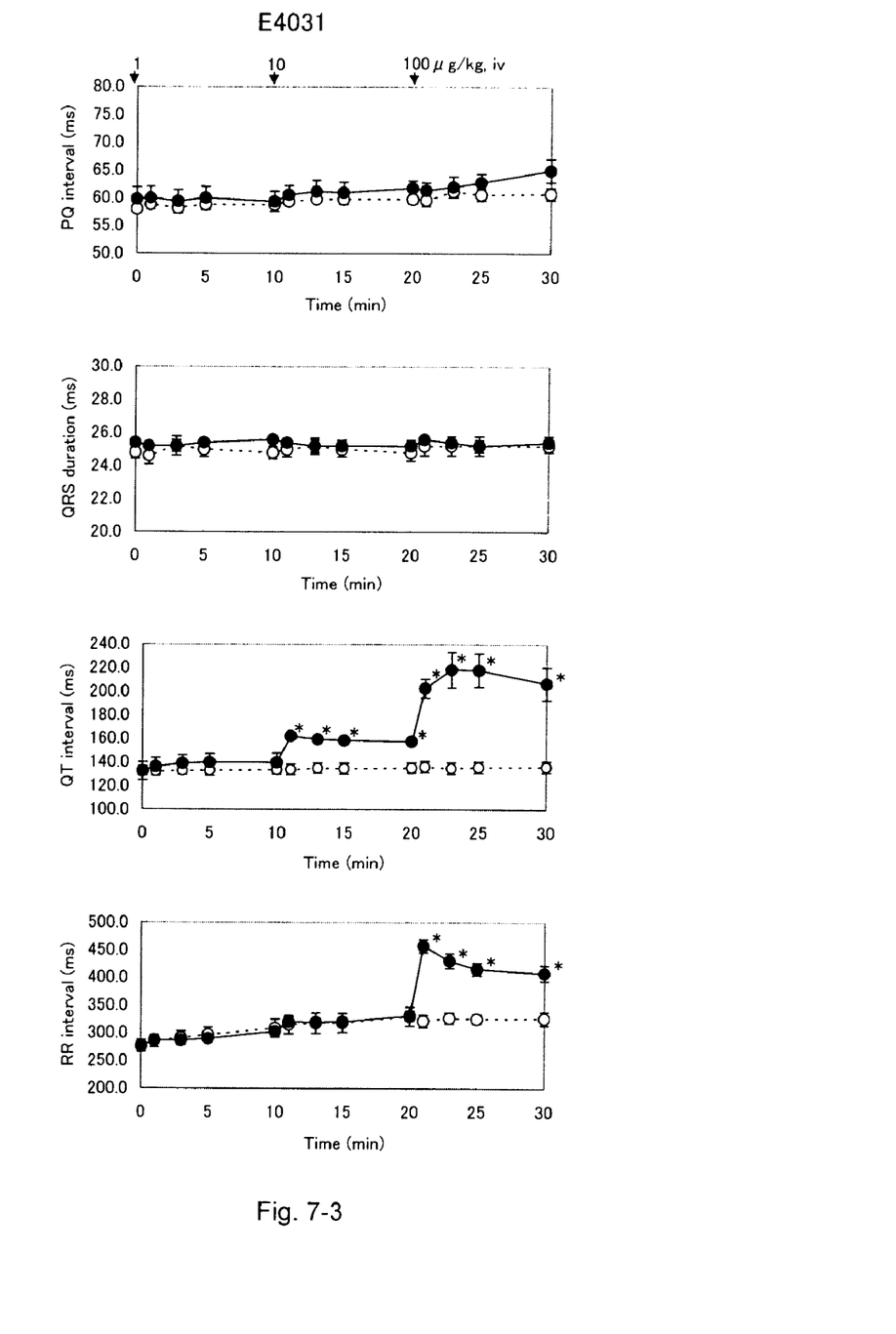

Influences of terfenadine, cisapride and E4031 on the electrocardiogram parameters are shown in FIGS. 7-1, 7-2 and 7-3, respectively. After the administration of 1 mg/kg of terfenadine, prolongation of the QT interval was observed. Degree of the prolongation was about 20%. Prolongation of the PQ interval was also observed simultaneously. It did not significantly affect the QRS interval and the RR interval.

Cisapride showed prolongation of the QT interval at 100 μg/kg, and the degree was about 20%. It did not significantly affect the PQ interval, the QRS interval and the RR interval.

E4031 significantly prolonged the QT interval at 10 μg/kg, and the degree was about 20%. At this dose, it did not significantly affect the RR interval. The QT interval was further prolonged at 100 μg/kg, and 50 to 60% of the prolongation was provided. Moreover, prolongation of the RR interval was also observed. It hardly affected the PQ interval and the QRS interval.

There is a report of an investigation on the QT prolongation actions of terfenadine, cisapride and E4031 based on duration of monophasic action potential using anesthetized dogs (Xenobiotica, 31, 633-650, 2001). On the basis of the results of this report, single doses for intravenous administration of terfenadine, cisapride and E4031 providing 10% of prolongation of the duration of monophasic action potential are calculated to be 300 μg/kg, 100 μg/kg and 10 μg/kg, respectively, and they substantially comparative to the results of this example. Therefore, it can be said that a hamster under mixed anesthesia with pentobarbital and xylazine shows substantially the same sensitivity as that of an anesthetized dog as an evaluation system for examination of the QT prolongation action based on $I_{Kr}$ suppression. In addition, after the administration of 1 mg/kg of terfenadine, prolongation of the PQ interval was also observed, and this is considered to be induced by the Ca antagonism of terfenadine (Cir. Res., 81, 202-210, 1997).

The above results demonstrate that a hamster under the mixed anesthesia has a property concerning these drugs similar to those of humans and anesthetized dogs.

INDUSTRIAL APPLICABILITY

Since the evaluation method of the present invention utilize a small animal, hamster, required amount of a test substance may be small. It is especially advantageous for evaluation of a compound at a stage that the compound can be obtained only in a small amount, such as in vivo evaluation of a compound at a searching stage. Moreover, many specimens can be examined more easily in view of experimental techniques compared with the method of using dogs conventionally generally used.

What is claimed is:

1. A method for evaluating electrocardiogram QT interval-prolonging action of a test substance, which comprises preparing a hamster anesthetized under such a condition that end of T wave is definitely observed on an electrocardiogram, and comparing electrocardiogram QT intervals of the anesthetized hamster observed before and after administration of the test substance to evaluate electrocardiogram QT interval-prolonging action of the test substance.

2. The evaluation method according to claim 1, wherein anesthetization is mixed anesthesia with pentobarbital and xylazine.

3. The evaluation method according to claim 2, wherein the pentobarbital is administered at a dose of 30 to 70 mg/kg and xylazine is administered at a dose of 1 to 3 mg/kg.

4. The evaluation method according to claim 1, wherein the hamster is 4 to 30 weeks old.

5. The evaluation method according to claim 1, wherein leads on the hamster's body surface are used.

6. The evaluation method according to claim 5, wherein standard limb lead I is used.

7. The evaluation method according to claim 5, wherein standard limb lead II is used.

8. The evaluation method according to claim 5, wherein unipolar limb lead VR is used.

9. The evaluation method according to claim 1, wherein the hamster is in the dorsal position.

10. The evaluation method according to claim 1, wherein the hamster is in the ventral position.

11. The evaluation method according to claim 1, which is conducted with an apparatus having a sensitivity of 10 to 100 mm/mV and a frequency characteristic of −6 dB at 0.08 Hz to 1 kHz.

* * * * *